United States Patent [19]

Detty et al.

[11] Patent Number: 5,500,317
[45] Date of Patent: Mar. 19, 1996

[54] ELECTROPHOTOGRAPHIC ELEMENTS CONTAINING SOLUBLE CYCLIC SULFONE ELECTRON TRANSPORT AGENTS

[75] Inventors: Michael R. Detty; John A. Sinicropi, both of Rochester; J. Robin Cowdery-Corvan, Webster; Ralph H. Young, Rochester, all of N.Y.

[73] Assignee: Eastman Kodak Company, Rochester, N.Y.

[21] Appl. No.: 260,846

[22] Filed: Jun. 16, 1994

[51] Int. Cl.$^6$ .................................................. G03G 5/047
[52] U.S. Cl. ............................................ 430/58; 430/75
[58] Field of Search .............................. 430/58, 75

[56] References Cited

U.S. PATENT DOCUMENTS

| | | | |
|---|---|---|---|
| 3,387,593 | 2/1968 | Mattson et al. | 514/326 |
| 3,615,414 | 10/1971 | Light . | |
| 4,175,960 | 11/1979 | Berwick et al. . | |
| 4,514,481 | 4/1985 | Scozzafava et al. . | |
| 4,578,334 | 3/1986 | Borsenberger et al. . | |
| 4,666,802 | 5/1987 | Hung et al. . | |
| 4,701,396 | 10/1987 | Hung et al. . | |
| 4,719,163 | 1/1988 | Staudenmayer et al. . | |
| 4,968,813 | 11/1990 | Rule et al. . | |
| 5,013,849 | 5/1991 | Rule et al. . | |
| 5,034,293 | 7/1991 | Rule et al. . | |
| 5,039,585 | 8/1991 | Rule et al. . | |
| 5,272,032 | 12/1993 | Cowdery et al. | 430/58 |
| 5,280,034 | 1/1994 | Hall et al. | 514/374 |
| 5,300,385 | 4/1994 | Detty et al. | 430/58 |
| 5,306,587 | 4/1994 | Terrell et al. | 430/58 |
| 5,346,907 | 9/1994 | Kerwin, Jr. et al. | 514/312 |
| 5,360,910 | 11/1994 | Huang et al. | 546/279 |
| 5,380,751 | 1/1995 | Chen et al. | 514/449 |
| 5,380,857 | 1/1995 | Roduit et al. | 546/273 |
| 5,386,031 | 1/1995 | DeJong et al. | 544/280 |
| 5,395,850 | 3/1995 | Roth | 514/471 |
| 5,399,561 | 3/1995 | Chandraratna | 514/252 |
| 5,412,092 | 5/1995 | Rey et al. | 540/200 |

OTHER PUBLICATIONS

*Grant and Hackh's Chemical Dictionary*, fifth edition, R. Grant et al. editors, McGraw–Hill, Inc., N.Y., pp. 53–290 (1987).
Detty et al., *J. Org. Chem.*, vol. 52, 1987, pp. 3662–3668.
Detty et al., *Tetrahedron*, vol. 41, No. 21, 1985, pp. 4853–4859.
Chen et al., *J. Org. Chem.*, vol. 51, 1986, pp. 3282–3289.

*Primary Examiner*—Christopher D. Rodee
*Attorney, Agent, or Firm*—Robert Luke Walker; Anne B. Kiernan

[57] ABSTRACT

A sulfone charge transport agent and a multilayered electrophotographic element in which at least one of said layers includes polymeric binder and the sulfone charge transport agent. The general structure of the charge transport agent is:

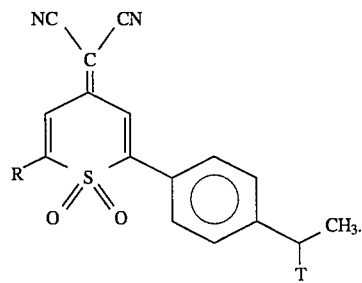

R is alkyl or cycloalkyl having from 1 to about 10 carbons, or aryl or heteroaryl having a total of carbons and heteroatoms of from 6 to about 12. T is alkyl having from 1 to 4 carbons.

20 Claims, No Drawings

ELECTROPHOTOGRAPHIC ELEMENTS CONTAINING SOLUBLE CYCLIC SULFONE ELECTRON TRANSPORT AGENTS

FIELD OF THE INVENTION

This invention relates to electrophotography, electrophotographic elements and cyclic sulfone compounds and more particularly relates to electron transport agents that are derivatives of 4H-thiopyran-1,1-dioxide which exhibit improved solubility and to electrophotographic elements that include those agents.

BACKGROUND OF THE INVENTION

In electrophotography an image comprising a pattern of electrostatic potential (also referred to as an electrostatic latent image), is formed on a surface of an electrophotographic element comprising at least two layers: an insulative photoconductive layer and an electrically conductive substrate. The electrostatic latent image can be formed by a variety of means, for example, by imagewise radiation-induced discharge of a uniform potential previously formed on the surface. Typically, the electrostatic latent image is then developed into a toner image by contacting the latent image with an electrographic developer. If desired, the latent image can be transferred to another surface before development.

The imagewise discharge is brought about by the radiation-induced generation of electron-hole pairs, by a material (often referred to as a charge-generation material) in the electrophotographic element. Depending upon the polarity of the initially uniform electrostatic potential and the type of materials in the electrophotographic element, either the holes or the electrons that have been generated migrate toward the charged surface in the exposed areas and cause the imagewise discharge of the initial potential. What remains is a non-uniform potential constituting the electrostatic latent image. Electrophotographic elements often have separate layers that can be identified as a charge generation layer (CGL) and a charge transport layer (CTL) on the basis of their primary functions.

Many electrophotographic elements are designed to be initially charged with a negative polarity. They contain material, known as a hole-transport agent, which facilitates the migration of positive holes toward the negatively charged surface in imagewise exposed areas. A positively charged toner is used to develop the unexposed areas. Because of the wide use of negatively charging elements, many types of positively charging toners are available.

For some applications, however, it is desirable to develop the exposed rather than the unexposed surface areas of the element. For example, in laser printing of alphanumeric characters it is more desirable to expose the small surface area that will form visible alphanumeric toner images, rather than waste energy exposing the large background area. In order to accomplish this with available high quality positively charging toners, it is necessary to use an electrophotographic element that is designed to be positively charged. Positive toner can then develop the exposed surface areas (which will have relatively negative electrostatic potential).

An electrophotographic element designed to be initially positively charged should contain an electron-transport agent, that is, a material which facilitates the migration of photogenerated electrons toward the positively charged surface. Unfortunately, while many good hole-transport agents are available, relatively few electron transport agents are known and many prior art compounds have one or more drawbacks.

In order for electron transport to occur in the CTL, two events are necessary. The first event is the capture of the electron injected by the CGL. The second event is the movement of electrons from one molecule to the next in the CTL. The former process affects the quantum yield for electron capture as measured in terms of electrophotographic speed under conditions of low-intensity continuous exposure, while the latter process represents the kinetics of electron exchange in the CTL as measured in terms of mobility.

Some previous electron-transport agents do not perform the electron transporting function well except under limited conditions or in limited types of electrophotographic elements. Some agents cause an undesirably high rate of discharge of the electrophotographic element before it is exposed, also referred to as high dark decay.

Some previous electron-transport compounds have limited solubility or dispersibility in coating solvents and limited compatibility in polymeric binders. Increasing the concentration of an electron-transport agent in a polymeric layer, in the absence of phase-separation, increases the electron-transport mobility of the layer; accordingly, photogenerated electrons move through the layer at a higher velocity and traverse the layer in a shorter period of time. The higher the mobility, the shorter is the waiting period between exposure and development, and the greater is the number of copies that can be made in a given amount of time. Even when sufficient amounts of electron-transport agent can be compatibly incorporated in an electrophotographic element during manufacture, problems can arise during use due to migration of the electron transport agent.

Among electron-transport materials, those molecules based on 1,1-dioxo-4H-4-(dicyanomethylidene) thiapyran-4-one (the "sulfones") have electron mobilities and electrophotographic speeds that are high relative to most electron-transport materials. U.S. Pat. Nos. 4,514,481 to Scozzafava et al; and 4,968,813; 5,013,849; 5,034,293; and 5,039,585 all to Rule et al; teach derivatives of 4H-thiopyran-1,1-dioxides. U.S. Pat. No. 4,514,481 discloses 4-dicyanomethylene-2,6-diphenyl-4H-thiopyran-1,1-dioxide (also referred to herein as DPS), which has the structural formula:

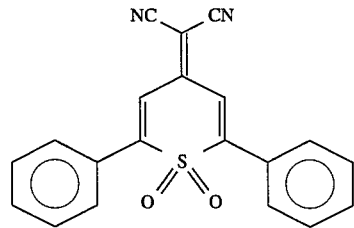

U.S. Pat. No. 5,039,585 discloses 4-dicyanomethylene-2-p-tolyl-6-phenyl-4H-thiopyran-1,1-dioxide (also referred to herein as PTS), which has the structural formula:

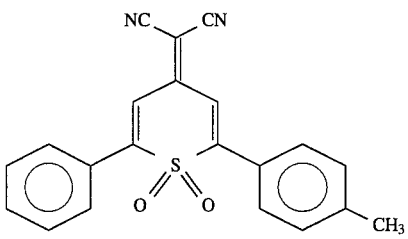

DPS and PTS have about the same electron mobilities, however, PTS is more soluble.

The terms "solubility" and "compatibility" are used herein to describe the ability of a first material to disperse in a second material so as to form a homogenous blend. The term "solubility" is generally used to describe the ability of a material to dissolve in liquid solvents to form a solution. The term "solubility" used herein, does not, however, exclude dispersions which appear to be homogeneous, at least to unmagnified examination. The term "compatibility" is generally used to describe the ability of a material to blend with a polymer so as to produce a material which appears to be homogeneous, at least to unmagnified examination. The term "miscibility" defines a similar concept. The terms "incompatible" and "incompatibility" and the like, used herein refer to an intermixture which is characterized by segregation of sulfone and polymer binder, that is, crystallization or aggregate formation which is visible without magnification. Such crystallization or aggregate formation causes such problems as undesirable dark decay, as well as scatter or absorption of actinic radiation intended to pass through the charge-transport layer.

U.S. Pat. No. 4,514,481 describes the incorporation of DPS and other similar sulfones in polymeric binder layers of electrophotographic elements at a concentration of 30% by weight (based upon the total weight of the agent and the binder) for good performance. The upper limit of compatibility (solubility or homogeneous dispersibility) of compounds such as DPS in many polymeric binders is about 40% by weight. At such concentrations, DPS and similar sulfones are on the edge of incompatibility and an elevation in temperature can cause migration within the binder and the formation of undesirable crystalline aggregates. This is a major shortcoming, since electrophotographic elements encounter elevated temperatures during normal use in a copier. PTS has a higher solubility than DPS in solvents useful for preparing a photoconductor. This allows higher loading levels in the final photoconductor composite, which in turn results in increased photogenerated charge migration, leading to potentially faster photodischarge speeds and lower toe/erase voltages. PTS has a compatibility limit of about 60% by weight. At that loading level, PTS has crystallization problems comparable to the problems seen with DPS at 40% loading.

Thus, there is a need for electrophotographic elements containing electron transport agents which have good electron mobilities and electrophotographic speeds and exhibit good solubility in coating solvents and good compatibility with polymeric film-forming binders and thus can be used at very high loading levels.

SUMMARY OF THE INVENTION

The invention, in its broader aspects, provides a sulfone charge transport agent and a multilayered electrophotographic element in which at least one of said layers includes polymeric binder and the sulfone charge transport agent. The general structure of the charge transport agent is:

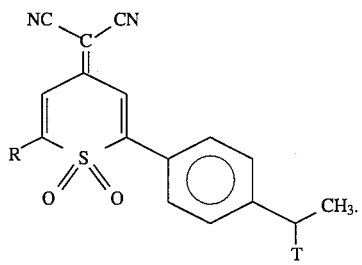

R is alkyl or cycloalkyl having from 1 to about 10 carbons, or aryl or heteroaryl having a total of carbons and heteroatoms of from 6 to about 12. T is alkyl having from 1 to 4 carbons.

It is an advantageous effect of at least some of the embodiments of the invention that the sulfones of the invention have both unexpectedly good compatibility with polymeric binders and solubility in solvents for those binders, and good electron-transport properties in electrophotographic elements of the invention.

DESCRIPTION OF PARTICULAR EMBODIMENTS

The electrophotographic elements of the invention have at least one layer that includes one or more of the sulfones of the invention, as charge transport agent. The sulfones of the invention have both good electron mobilities and good solubility in coating solvents and compatibility with film-forming polymeric binders. In particular embodiments of the invention, disclosed in detail herein, the electron mobility of the sulfone of the invention is about the same as that of PTS and the solubility in coating solvents and compatibility with polymer binders are higher than for PTS. As is shown by the examples below, in the sulfones of the invention, and such other sulfones as PTS, there is an empirical correlation between compatibility of a sulfone with a polymer binder and solubility of the sulfone in a solvent for that polymer binder. The high solubility and compatibility of the sulfones of the invention presents advantages, at high charge transport agent loading levels; both during manufacture of an electrophotographic element, in ease of use of coating solutions; and during use of the element, in increased photogenerated charge migration, which can lead to faster photodischarge speeds and lower toe/erase voltages.

The sulfones of the invention have the general structure:

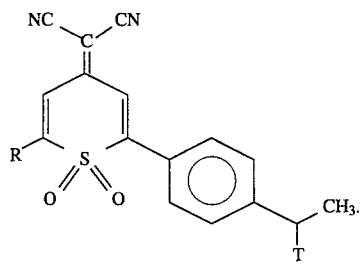

T is alkyl having from 1 to 4 carbons. R is alkyl or cycloalkyl having from 1 to about 10 carbons; aralkyl or heteroaralkyl having a from 1 to about 4 carbon alkene moiety and a five or six membered aromatic or heteroaromatic ring; or aryl or heteroaryl having a total of carbons and heteroatoms of from 6 to about 12. The backbone or ring system of R can be unsubstituted or can be substituted by alkyl having from 1 to about 12 carbons, alkoxy having from 1 to about 12 carbons, nitro, cyano, dialkylamino, arylalkylamino, and diarylamino.

In a preferred embodiment of the invention, R is an aromatic or heteroaromatic ring system having a single ring or two linked or fused rings. Suitable aliphatic R groups include: methyl, ethyl, propyl, isopropyl, butyl, isobutyl, t-butyl, pentyl, hexyl, 2-ethylhexyl, cyclopentyl, cyclohexyl, 4-methylcyclohexyl, and octyl. Suitable aralkyl groups include: benzyl and phenethyl. Suitable aromatic and heteroaromatic R groups include: phenyl, naphthyl, 2-thienyl, 3-thienyl, 2-furyl, 5-methyl-2-thienyl, and 2-selenophene. Examples of specific sulfones of the invention are:

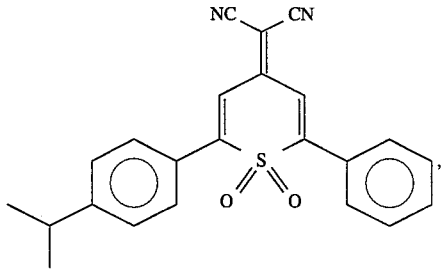

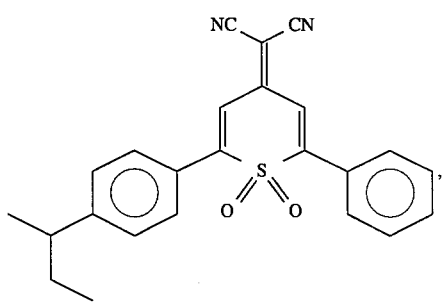

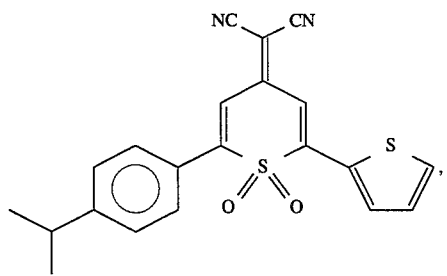

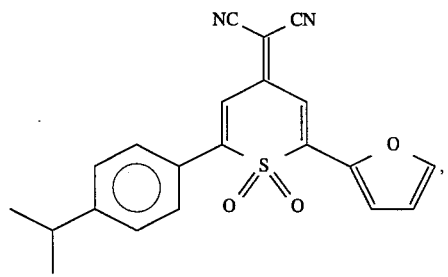

-continued

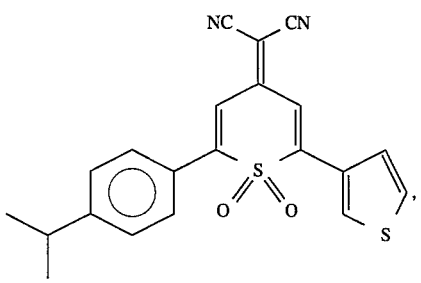

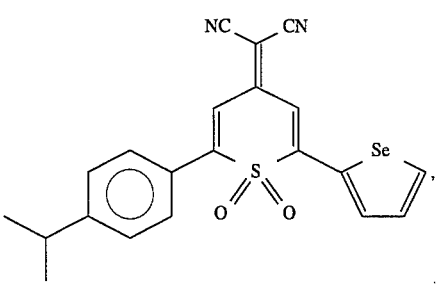

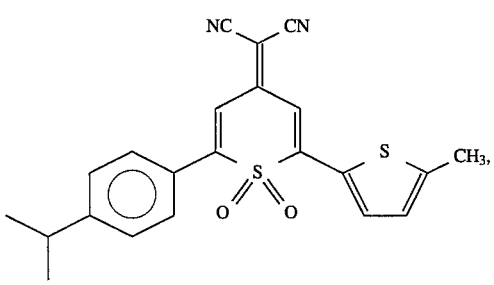

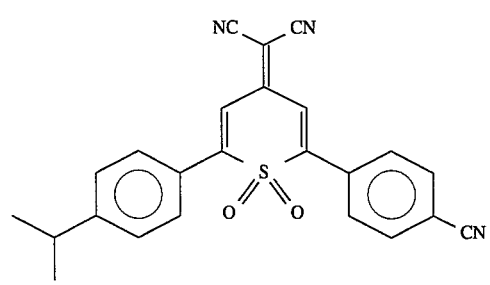

The sulfones of the invention, can be prepared from 1,5-disubstituted-1,4-pentadiyn-3-ones by the following scheme:

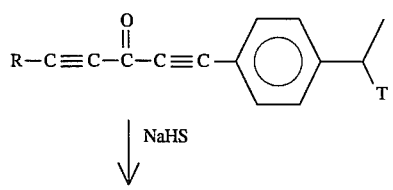

↓ NaHS

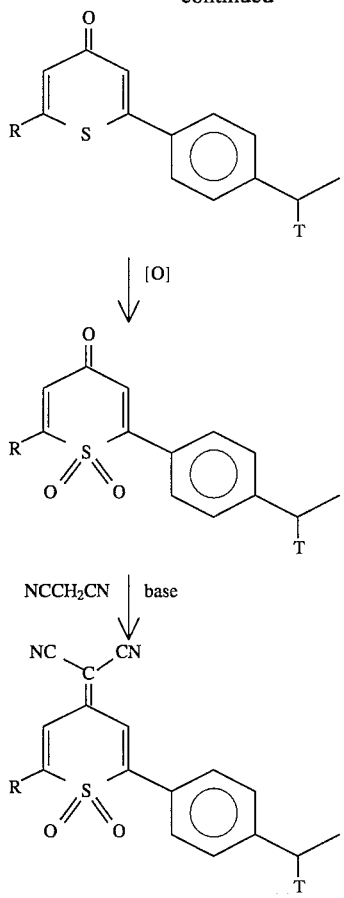

A route to 1,5-disubstituted-1,4-pentadiyn-3-ones is described by Detty et al., *J. Org. Chem.*, 1987, Vol. 52, p. 3662. The reaction of substituted 1,4-pentadiyn-3-ones with sodium hydrosulfide to produce 1-thiopyran-4-ones is described by Detty et al., *Tetrahedron*, (1985), Vol. 41, pp. 4853–4859. Conversion of thiopyranones to the corresponding 1,1-dioxides by oxidizing agents such as peracetic acid and reaction of the dioxides with malononitrile under basic conditions are disclosed in U.S. Pat. No. 4,514,481, which is hereby incorporated herein by reference.

The substituted 1,4-pentadiyn-3-ones required to prepare the electron-transport agents of the invention can be synthesized by the reaction of alkyl-, aralkyl-, or cycloalkyl-substituted alkynyl lithium compounds with aryl-substituted propargyl aldehydes to yield 1,4-pentadiyn-3-ols, which are then oxidized by reagents such as chromic acid to the corresponding diynones. This is illustrated by the following scheme:

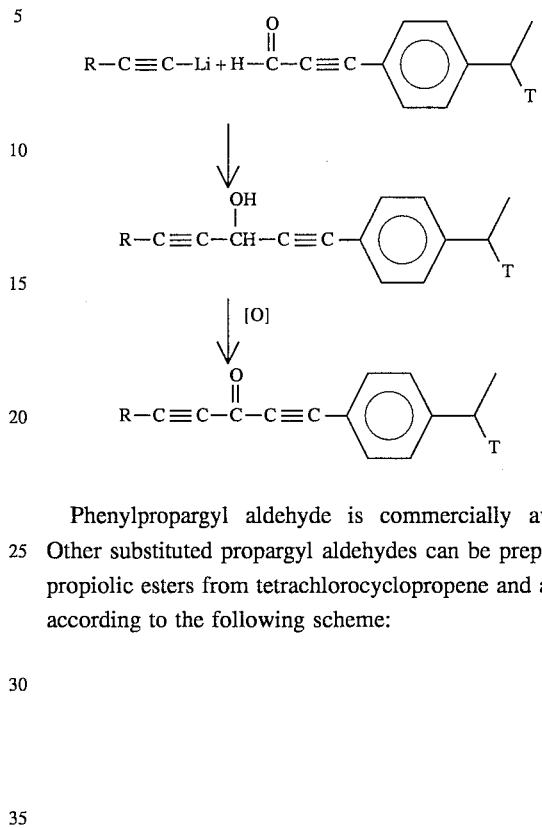

Phenylpropargyl aldehyde is commercially available. Other substituted propargyl aldehydes can be prepared via propiolic esters from tetrachlorocyclopropene and an arene according to the following scheme:

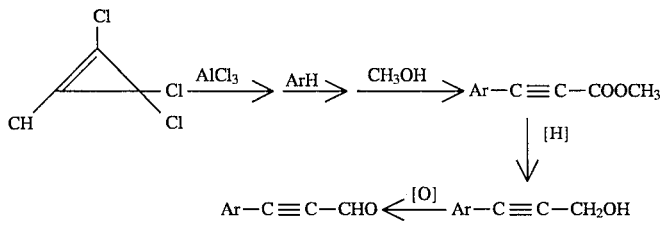

The reduction of propiolic esters to propargyl alcohols can be effected by hydride reducing agents, for example, diisobutylaluminum hydride. For oxidation of propargyl alcohols to the corresponding aldehydes, pyridinium chlorochromate is a suitable reagent.

The reaction scheme previously described is best suited for the preparation of 6-alkyl-2-aryl sulfones. For 2,6-diaryl sulfones and 2-heteroaryl-6-aryl sulfones, the following reaction scheme is preferred:

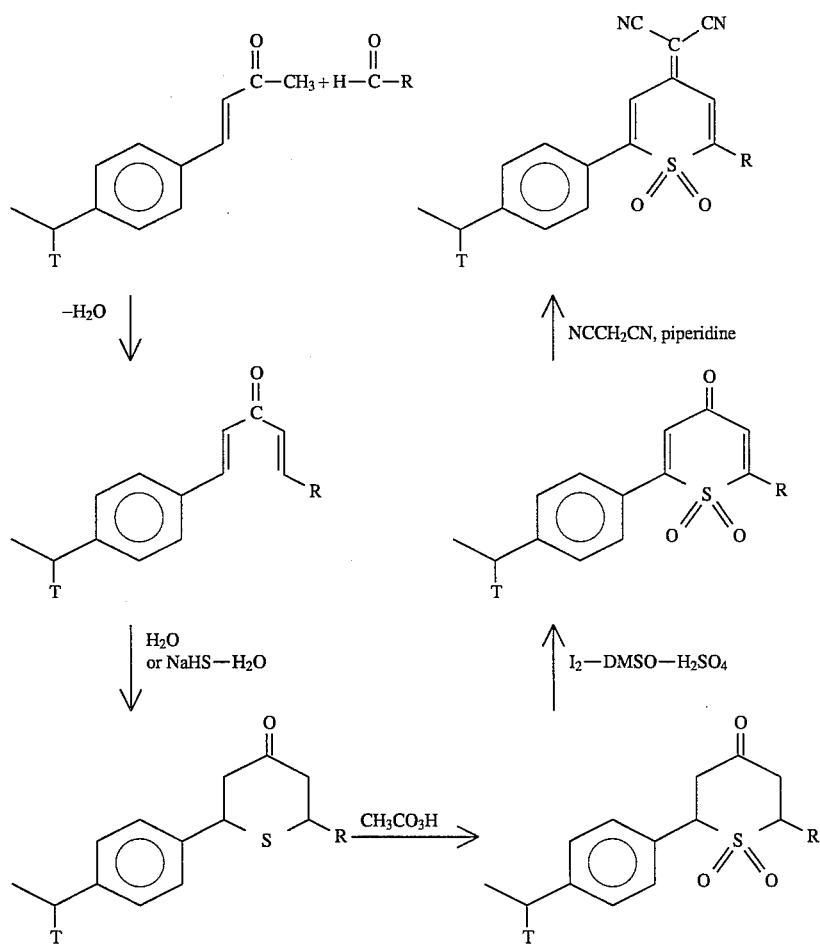

Similar approaches to DPS and PTS have been described in Chen, et al, *J. Org. Chem.*, Vol. 51, (1986) p. 3282; and U.S. Pat. No. 4,514,481 to Scozzafava et al; and U.S. Pat. No. 5,039,585 to Rule et al. The starting material having the general structure:

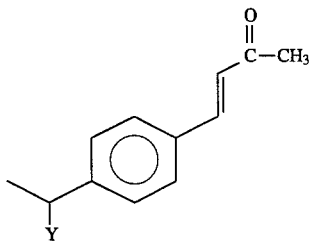

can be produced by condensation of a 4-alkyl benzaldehyde with excess acetone.

The new electrophotographic elements of the invention can be of various types, all of which contain one or more of the sulfones of the invention as electron-transport agents in one or more layers of the elements. The various types of elements in accordance with the present invention include both those commonly referred to as single layer or single-active-layer elements and those commonly referred to as multiactive, or multi-active-layer elements. All of the electrophotographic elements of the invention have multiple layers, since each element has at least an electrically conductive layer and one other layer.

Single-active-layer elements are so named because they contain only one layer that is active both to generate and to transport charges in response to exposure to actinic radiation. Such elements have an additional electrically conductive layer in electrical contact with the photoconductive layer. In single-active-layer elements of the invention, the photoconductive layer contains a charge-generation material to generate electron/hole pairs in response to actinic radiation and an electron-transport material, comprising one or more of the sulfones of the invention, which is capable of accepting electrons generated by the charge-generation material and transporting them through the layer to effect discharge of the initially uniform electrostatic potential. The photoconductive layers of single-active-layer electrophotographic elements usually contain from about 0.01 to 50 weight percent of charge-generating material. The photoconductive layer is electrically insulative except when exposed to actinic radiation. The photoconductive layer can contain an electrically insulative polymeric film-forming binder which is itself the charge-generating material. Alternatively, the photoconductive layer contains both a charge generating material and a polymeric binder that is not charge-generating. In either case, the electron-transport agent, the sulfone of the invention, is dissolved or dispersed as uniformly as possible in the photoconductive layer.

Multiactive layer elements are so named because they contain at least two active layers, at least one of which is capable of generating charge, that is, electron/hole pairs, in response to exposure to actinic radiation and is therefore referred to as a charge-generation layer (CGL), and at least one of which is capable of accepting and transporting charges generated by the charge-generation layer and is therefore referred to as a charge-transport layer (CTL). Such elements typically comprise at least an electrically conductive layer, a CGL, and a CTL. Either the CGL or the CTL is in electrical contact with both the electrically conductive layer and the remaining CTL or CGL. The CGL contains a charge-generation material. If the charge-generation material is not also a polymeric binder, then a polymeric binder can also be present. The CTL contains a charge-transport agent, which is the sulfone of the invention, and a polymeric binder.

Single-active-layer and multiactive layer electrophotographic elements and their preparation and use in general, are well known and are described in more detail, for example, in U.S. Pat. Nos. 4,701,396; 4,666,802; 4,578,334; 4,719,163; 4,175,960; 4,514,481 and 3,615,414, the disclosures of which are incorporated herein by reference.

In preparing the electrophotographic elements of the invention, the components of the photoconductive layer (in single-active-layer elements) or CTL (in multiactive layer elements), including any desired addenda, are dissolved or dispersed together in a liquid and then coated over an appropriate underlayer. The underlayer can be an electrically conductive layer, or support or, with a multiactive layer element, the CGL. The liquid is then allowed or caused to evaporate from the mixture to form the permanent photoconductive layer or CTL. The weight percent of charge transport agent in the completed photoconductive layer or CTL does not differ substantially from the weight percent of the charge transport agent in the total of polymer binder and sulfone present in the coating solution.

The ratio of charge transport agent to binder or of charge-transport agent and charge generation material to binder can be varied widely, depending on the particular materials employed. In the electrophotographic elements of the invention, useful results can be obtained when the amount of active charge transport agent or charge generation material or both contained within a layer is greater than about 10 weight percent and less than about 90 weight percent. (The percentage of charge generating material will vary if the charge-generating material is also the binder.) In many uses a desirable minimum concentration of charge transport agent is about 20 weight percent and an even better minimum concentration is about 40 weight percent. A desirable maximum concentration is well below the upper limit of compatibility seen during preparation of the electrophotographic element. The reason is that during use, the maximum limit of compatibility effectively drops. For example, a desirable range for the concentration of PTS in an electrophotographic element is about 40 to 50 weight percent; since an element having more than 50 weight percent PTS can exhibit zones of incompatibility, i.e., crystallinity, after moderate electrophotographic use. An electrophotographic element having a sulfone of the invention, rather than PTS, has much greater compatibility and is thus more resistant to crystallization. Thus, a preferred range of concentration for the sulfone:

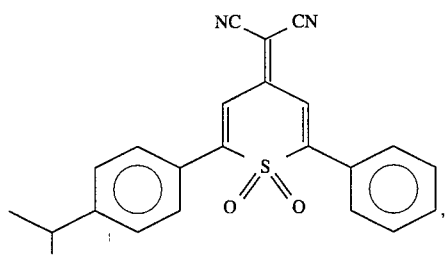

in an electrophotographic element of the invention, is from 40 to 70 weight percent and a preferred range of concentration of the sulfone:

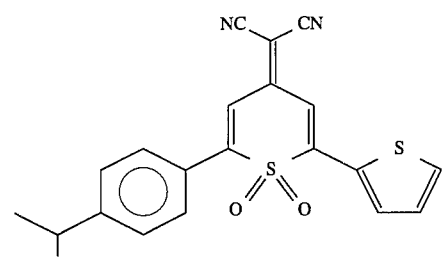

is from 40 to 60 weight percent.

The polymeric binder in the layer containing the sulfone of the invention is a film-forming polymer that preferably also has good electrically insulating properties. The film forming characteristics of the polymer can present a practical limit on the amount of sulfone that can be present in the CTL or photoconductive layer. Too high a concentration of sulfone may cause the layer to be excessively soft or friable making it unusable. Binder polymers should provide little or no interference with the transport; and in single active layer elements, the generation; of charges in the layer. The binder polymer can also be selected to provide additional functions. For example, adhering the sulfone containing layer to an adjacent layer; or, as a top layer, providing a smooth, easy to clean, wear-resistant surface. Examples of suitable polymeric binders include: styrene-butadiene copolymers; vinyl-toluene-styrene copolymers; styrene-alkyd resins; silicone-alkyd resins; soya-alkyd resins; vinylidene chloride-vinyl chloride copolymers; poly(vinylidene chloride); vinylidene chloride-acrylonitrile copolymers; vinyl acetate-vinyl chloride copolymers; poly(vinyl acetals), such as poly(vinyl butyral); nitrated polystyrene; poly(methylstyrene); isobutylene polymers; polyesters, such as poly[ethylene-co-alkylenebis(alkyleneoxyaryl) phenylenedicarboxylate]; phenol-formaldehyde resins; ketone resins; polyamides; polycarbonates; polythiocarbonates; poly-[ethylene-co-isopropylidene-2,2-bis (ethyleneoxy-phenylene)terephthalate]; copolymers of vinyl haloacrylates and vinyl acetate; chlorinated polyolefins such as chlorinated polyethylene; and polyimides, such as poly[1,1,3-trimethyl-3-(4'-phenyl)-5-indane pyromellitimide]. Examples of binder polymers which are particularly desirable from the viewpoint of minimizing interference with the generation or transport of charges include: bisphenol A polycarbonates and polyesters such as poly[(4,4'-norbornylidene)diphenylene terephthalate-co-azelate].

The choice of a polymeric binder, to some extent defines the choices of solvent to be used in preparing the sulfone containing layer. The sulfone and binder must both be soluble in the solvent and the solvent must have acceptable characteristics relative to any underlayer. The solvent, for example, should not dissolve away the underlayer and should provide for good bonding between the two layers. Health and safety concerns and convenience are additional considerations. Included among many useful solvents for this purpose are, for example, aromatic hydrocarbons such as benzene, toluene, xylene and mesitylene; ketones such as acetone and butanone; halogenated hydrocarbons such as dichloromethane, trichloroethane, chloroform, and ethylene chloride; ethers, including ethyl ether and cyclic ethers such as tetrahydrofuran, other solvents such as acetonitrile; and mixtures thereof.

The polymeric binders useful for the sulfone containing layer can also be used in producing a CGL. Any charge-generation material can be utilized in elements of the invention. Such materials include inorganic and organic (including monomeric organic, metallo-organic and polymeric organic) materials, for example, zinc oxide, lead oxide, selenium, or phthalocyanine, perylene, arylamine, polyarylalkane, and polycarbazole materials, among many others.

CGL's and CTL's in elements of the invention can optionally contain other addenda such as leveling agents, surfactants, plasticizers, sensitizers, contrast control agents, and release agents, as is well known in the art.

Various electrically conductive layers or supports can be employed in electrophotographic elements of the invention, for example, paper (at a relative humidity above 20 percent) aluminum-paper laminates; metal foils such as aluminum foil, zinc foil, etc.; metal plates such as aluminum, copper, zinc, brass and galvanized plates; vapor deposited metal layers such as silver, chromium, vanadium, gold, nickel, aluminum and the like; and semiconductive layers such as cuprous iodide and indium tin oxide. The metal or semiconductive layers can be coated on paper or conventional photographic film bases such as poly(ethylene terephthalate), cellulose acetate, polystyrene, etc. Such conducting materials as chromium, nickel, etc. can be vacuum-deposited on transparent film supports in sufficiently thin layers to allow electrophotographic elements so prepared to be exposed from either side.

Electrophotographic elements of the invention can include various, as optional layers, any of the additional layers known to be useful in electrophotographic elements in general, for example, subbing layers, overcoat layers, barrier layers, and screening layers.

The following preparations and examples are presented to further illustrate some specific electrophotographic elements of the invention and chemical compounds useful as electron-transport agents therein. Melting points were determined on a Thomas-Hoover melting point apparatus and are uncorrected. $^1$H NMR spectra were recorded either on a General Electric QE-300 spectrometer or on a Varian Gemini-200 spectrometer. UV-visible-near infrared spectra were recorded on a Perkin-Elmer Lambda 9 spectrophotometer. Infrared spectra were recorded on a Beckman IR 4250 instrument or a Perkin-Elmer 298 infrared spectrophotometer. Microanalyses were performed on a Perkin-Elmer 240 C, H, and N Analyzer.

EXAMPLE 1

The procedures given below and in Example 2 are representative of those used to prepare the sulfones of the invention.

Preparation of E,E-1-(p-isoproplphenyl)-5-(2-thienyl)-1,4-pentadine-3-one:

A mixture of 7.9 grams (0.042 mol) of E-4-(p-isopropylphenyl)-3-butene-2-one, 4.7 grams (0.042 mol) of 2-thiophene carboxaldehyde, 2 mL of 10% sodium hydroxide, 30 mL of water, and 75 mL of ethanol was stirred at ambient temperature for 15 hours. The product was collected by filtration and air dried to give 10.2 grams (86% of theoretical yield) of E,E-1-(p-isopropylphenyl)-5-(2-thienyl)-1,4-pentadien-3-one as a yellow solid. Melting point was determined to be 100°–101° C. Proton nuclear magnetic resonance ($^1$H NMR) was conducted in CDCl$_3$: d 7.84 (d, 1H, J=16 Hz), 7.69 (d, 1H, J=16 Hz), 7.53 (AA'BB', 2H), 7.39 (m, 1H), 7.32 (m, 1H), 7.25 (AA'BB, 2H), 7.06 (dxd, 1H, J=3.6, 5 Hz), 6.96 (d, 1H, J=16 Hz), 6.87 (d, 1H, J=16 Hz), 2.90 (septet, 1H, J=7 Hz), 1.23 (d, 6H, J=7 Hz). Infrared spectroscopy was conducted using a KBr pellet: 2960, 1650, 1585, 1180, and 705 cm$^{-1}$. Field desorption mass spectral analysis (FDMS) was consistent with the proposed formula ($C_{18}H_{18}OS$) m$^+$/z 316.

Preparation of 2,3,5,6-Tetrahydro-2-(p-isopropylphenyl)-6-(2-thienyl)thiapyran-4-one:

A solution of 35.0 grams (0.124 mol) of E,E,-1-(p-isopropylphenyl)-5-(2-thienyl)-1,4-pentadien-3-one, 8 grams of sodium acetate, and 400 mL of ethanol was heated on a steam bath in a flask equipped with mechanical stirring, water-cooled reflux condenser, and gas inlet tube. Hydrogen sulfide gas was slowly bubbled into the reaction mixture until the pentadienone was consumed. The reaction mixture was cooled to ambient temperature and was diluted with 2 liters of water. The aqueous phase was extracted with dichloromethane 4 times using 300 mL each time. The combined organic extracts were washed with brine, dried over magnesium sulfate, and concentrated. The solid residue (35 grams, 90% of theoretical yield), believed to represent a mixture of diastereomers, was used without further purification. FDMS was consistent with the proposed formula ($C_{18}H_{20}OS_2$) m$^+$/z 316.

Preparation of 1,1-Dioxo-2,3,5,6-tetrahydro-2-(p-isopropylphenyl)-6-(2-thienyl)thiapyran-4-one:

30% Peracetic acid (120 mL) was added dropwise to a solution of 2,3,5,6-tetrahydro-2-(p-isopropylphenyl)-6-(2-thienyl)thiapyran-4-one (35.0 grams, 0.111 mol) and 8 grams of anhydrous sodium acetate in 300 mL of dichloromethane. After addition was complete, the reaction mixture was stirred for 1 hour at ambient temperature and was then diluted with 500 mL of water. The organic phase was separated and the aqueous phase was extracted with an additional 300 mL of dichloromethane. The combined organic extracts were washed with dilute sodium hydroxide solution, dried over magnesium sulfate, and concentrated to give 30.0 grams (80% of theoretical yield) of an oily residue that was used without further purification. $^1$H NMR (CDCl$_3$) was: d 7.50–7.00 (m, 7H), [4.86 (dxd), 4.74 (t){1 H}], 4,52 (m, 1H), 3.8–2.8 (m, 5H), 1.23 (d, 6H, J=7 Hz). FDMS was consistent with ($C_{18}H_{20}O_3S_2$): m$^+$/z 348.

Preparation of 4H-1,1-Dioxo-2-(p-isopropylphenyl)-6-(2-thienyl)thiapyran-4-one:

A solution of 25.0g (0.0718 mol) of 1,1-dioxo-2,3,5,6-tetrahydro-2-(p-isopropylphenyl)-6-(-2-thienyl)thiapyran, 130 mL of dimethylsulfoxide, 3.0 grams of iodine, and 2 mL of concentrated sulfuric acid was heated on a steam bath with mechanical stirring for 4 hours. The reaction mixture was cooled to ambient temperature and was diluted with 1 liter of water. The products were extracted with dichloromethane 4 times, using 200 mL each time. The combined organic extracts were washed with brine, dried over magnesium sulfate, and concentrated. The residue was slurried with ethanol and the resulting solid was collected by filtration and dried to give 20.0 grams (81% of theoretical yield) of a dark solid. Melting point was determined to be 92.0°–93.5° C. $1^H$ NMR (CDCl$_3$) was: d 7.95 (dxd, 1H, J=1, 4 Hz), 7.54 (AA'BB', 2H), 7.61 (dxd, 1H, J=1, 5 Hz), 3.54 (AA'BB', 2H), 7.20 (dxd, 1H, J=4, 5 Hz), 6.74 (d, 1H, J=2.7 Hz), 6.67 (d, 1H, J=2.7 Hz), 2.96 (septet, 1H, J=7 Hz), 1.27 (d, 6H, J=7 Hz). IR (KBr) was: 2960, 1680, 1585, 1415, 1305, 1135 and 710 cm$^{-1}$. FDMS was consistent with (C$_{18}$H$_{16}$O$_3$S$_2$) : m$^+$/z 344. Elemental analysis found C=62.42; H=4.74. This compares to calculated values for C$_{18}$H$_{16}$O$_3$S$_2$ of C=62.77; H=4.68.

Preparation of 4H-1,1-Dioxo-2-(p-isopropylphenyl)-6-(2-thienyl)-4-(dicyanomethyl-idene)thiapyran:

A mixture of 19.1 grams (0.0555 mol) of 4H-1,1-dioxo-2-(p-isopropylphenyl)-6-(2-thienyl)thiapyran-4-one and 7.5 grams (0.114 mol) of malononitrile in 160 mL of ethanol was heated at reflux with mechanical stirring. To this solution, a solution of 0.50 mL of piperidine in 40 mL of ethanol was added dropwise via pressure equalizing addition funnel. After 4 hours at reflux, the reaction mixture was cooled to ambient temperature. The crystalline solid was collected by filtration and washed with 100 mL of ethanol. The solid was heated to boiling in ethyl acetate/ethanol and filtered to provide 12.0 grams (55% of theoretical yield) of a burnt-orange crystalline solid. Melting point=199°–201° C. 1H NMR (CDCl$_3$) was: d 7.99 (dxd, 1H, J=1, 4 Hz), 7.78 (AA'BB', 2H), 7.67 (dxd, 1H, J=1, 5 Hz), 7.37 (AA'BB', 2H), 7.32 (d, 1H, J=2.6 Hz), 7.26 (d, 1H, J=2.6 Hz), 7.225 (dxd, 1H, J=4, 5 Hz), 2.97 (septet, 1H, J=7 Hz), 1.27 (d, 6H, J=7 Hz); IR (KBr) 2225, 1305, and 1135 cm$^{-1}$. FDMS was consistent with (C$_{21}$H$_{16}$N$_2$O$_2$S$_2$): m$^+$/z 392. Elemental analysis found: C=64.26; H=4.16; N=7.19. This compares to calculated values for C$_{21}$H$_{16}$N$_2$O$_2$S2 of C=64.26; H=4.11; N=7.14.

Saturated solutions of the sulfone of this example were prepared in toluene and dichloromethane at ambient temperature (approx. 23° C.) to determine maximum solubility. Results are presented in Table 1.

EXAMPLE 2

The following procedures were followed:
Preparation of E,E-1-(p-isopropylphenyl)-5-phenyl-1,4-pentadien-3-one:

A mixture of 81.0 grams (0.555 mol) trans-4-phenyl-3-buten-2-one, 81.7 grams (0.552 mol) 4-isopropylbenzaldehyde, 12 mL of 10% sodium hydroxide, 150 mL water and 220 mL ethanol was stirred at ambient temperature for 15 hours. The crystalline product was collected by vacuum filtration to give 90.0 grams (59% of theoretical yield) of E,E-1-(p-isopropylphenyl)-5-phenyl-1,4-pentadien-3-one as a yellow solid. Melting point=76.0°–78.0° C. IR (KBr) 2960, 1655, 1595, 1345, 1195, 980, 820, 760, 695 cm$^{-1}$; FDMS, m$^+$/z 276 (C$_{20}$H$_2$O). $^1$H NMR (CDCl$_3$) d 7.74 (d, 2H, J=16 Hz), 7.59 (m, 2H) , 7.55 (d, 2H, J=8 Hz) , 7.39 (m, 3H) , 7.26 (d, 2H, J=8 Hz), 7.09 (d, 1H, J=16 Hz), 7.045 (d, 1H, J=16 Hz), 2.93 (septet, 1,H, J=7 Hz), 1.26 (d, 6H, J=7 Hz). Anal. Calcd. for C$_{20}$H$_{20}$O; C, 86.92;H, 7.29. Found: C, 86.87,H, 7.32.

Preparation of 2,3,5,6-Tetrahydro-2-(p-isopropylphenyl)-6-phenylthiopyran-4-one:

A solution of 90.0 grams (0.326 mol) of E,E,-1-(p-isopropylphenyl)-5-phenyl-l,4-pentadien-3-one, 15.0 g anhydrous, sodium acetate, 200 mL ethanol and 50 mL dimethylformamide was heated on a steam bath in a flask equipped with a mechanical stirring device, a water-cooled reflux condenser and a gas inlet tube. Hydrogen sulfide gas was slowly bubbled into the reaction mixture until the pentadienone was consumed. The reaction mixture was cooled to ambient temperature and diluted with 1 L water. The aqueous phase was extracted with dichloromethane (4×125 mL). The combined organic extracts were dried over magnesium sulfate and concentrated. The resulting oily residue (90.0 g 89% of theoretical yield), a mixture of diastereomers, was used without further purification. FDMS, m$^+$/z 310 (C$_{20}$H$_{22}$OS). $^1$H NMR (CDCl$_3$) d 7.1–7.5 (m, 9H), 4.3 (m, 2H), 2.95 (m, 5H), 1.25 (d, 6H, J=7 Hz.)

Preparation of 1,1-Dioxo-2,3,5,6-tetrahydro-2-(p-isopropylphenyl)-6-phenylthiapyran-4-one:

32% Peracetic acid (125 mL) was added dropwise with frequent stirring to a solution of 2,3,5,6-Tetrahydro-2-(p-isopropylphenyl)-6-phenylthiapyran- 4-one (90.0 grams, 0.290 mol) and 15.0 grams of anhydrous, sodium acetate in 350 mL dichloromethane. After addition was complete, the reaction mixture was stirred for 1 hour at ambient temperature and then diluted with 1 L water. The aqueous phase was neutralized with a 10% solution of sodium hydroxide and solid sodium bicarbonate. The organic phase was separated and the aqueous phase was extracted with an additional 250 mL of dichloromethane. The combined organic extracts were dried over magnesium sulfate and concentrated to give 90.0 grams (91% of theoretical yield) of an oily residue that was used without further purification. FDMS, m$^+$/z 342 (C$_{20}$H$_{22}$O$_3$S) . $^1$H NMR (CDCl$_3$) d 7.0–7.5 (m, 9H), 4.5 (m, 1H), 3.72 (m, 1H), 2.9 (m, 5H), 1.25 (d, 6H, J=7 Hz).

Preparation of 4H-1,1-Dioxe-2-(p-isopropylphenyl)-6-phenylthiapyran-4-one:

A solution of 90.0 grams (0.263 mol) of 1,1-Dioxo-2,3, 5,6-tetrahydro-2-(p-isopropylphenyl)-6-phenylthiapyran-4-one, 110 mL methyl sulfoxide, 3.0 grams of iodine and 2.0 mL of concentrated sulfuric acid was heated on a steam bath for 4 hours. The reaction mixture was cooled to ambient temperature and diluted with 1 L water. The aqueous phase was neutralized with a 10% solution of sodium hydroxide and the organic phase was extracted into dichloromethane (4×125 mL). The combined organic extracts were dried over magnesium sulfate and concentrated to an oily residue. Ethanol (200 mL) was added to the oil. Combined stirring and cooling produced a crystalline solid collected by vacuum filtration and dried to give 67.2 g (76%) of a yellow solid. Melting point=86.0°–89.0° C. IR (KBr) 2965, 1655, 1595, 1310, 1135, 840, 770, 695 cm$^{-1}$. FDMS, m$^+$/z 338 (C$_{20}$H$_{18}$O$_3$S). $^1$H NMR (CDCl$_3$) d 7.82 (m, 2H), 7.76 (d, 2H, J=8 Hz), 7.53 (m, 3H), 7.36 (d, 2H, J=8 Hz), 6.68 (d, 1H, J=3 Hz), 1.25 (d, 6H, J=7 Hz). Anal. Calcd. for C$_{20}$H$_{18}$O$_3$S: C, 70.98;H, 5.36. Found: C, 70.63,H, 5.34.

Preparation of 4H-1,1-Dioxo-2-(p-isopropylphenyl)-6-phenyl-4-(dicyanomethylidene)thiapyran:

A mixture of 67.2 grams (0.199 mol) of 4H-1,1-Dioxo-2-(p-isopropylphenyl)-6-phenylthiapyran-4-one and 15.0 g (0.227 mol—a slight excess) of malononitrile in 110 mL ethanol was heated at reflux on a steam bath in a flask equipped with mechanical stirring and a water-cooled condenser w/dry tube. To this mixture, a solution of 0.50 mL piperidine in 20 mL ethanol was added dropwise via a pressure equalizing addition funnel. The reaction mixture refluxed approximately 4 hours, during which time all solids gradually dissolved and precipitated a yellow crystalline solid. The reaction mixture was cooled to ambient temperature and the product was collected by vacuum filtration and washed with 100 mL ethanol. The solid was heated to boiling in ethyl acetate/ethanol, cooled to ambient temperature and vacuum filtered to give 50.0 grams (66% of theoretical yield) of a bright yellow crystalline solid. Melting point=157.0°–159.0° C. IR (KBr) 2980, 2225, 1305, 1140, 835, 770, 690 cm$^{-1}$. FDMS, m$^+$/z 386

($C_{23}H_{18}N_2O_2S$). $^1$H NMR (CDCl$_3$) d 7.82 (m, 4H), 7.58 (m, 3H), 7.40 (d, 2H, J=8 Hz), 7.32 (d, 1H, J=2 Hz), 7.30 (d, 1H, J=2 Hz), 3.00 (septet, 1H, J=7 Hz), 1.30 (d, 6H, J=7 Hz). Anal Calcd. for $C_{23}H_{18}N_2O_2S$: C, 71.48;H, 4.69, N, 7.25. Found: C, 70.93;H, 4.82, N, 7.08.

Saturated solutions of the sulfone of this example were prepared in toluene and dichloromethane at ambient temperature (approx. 23° C.) to determine maximum solubility. Results are presented in Table 1.

COMPARATIVE EXAMPLES A–C

Saturated solutions of PTS, 4H-1,1-dioxo-2-(4-ethylphenyl)-6-(2-methylphenyl-4-(dicyanomethylidene)thiapyran and 4H-1,1-dioxo-2-(5-methylthienyl)-6-(4-ethylphenyl) (Comparative Examples A, B, and C, respectively) were prepared in toluene and dichloromethane at ambient temperature (approx. 23° C.) to determine maximum solubility. Results are presented in Table 1.

TABLE 1

| Example or Comparative Ex: Compound | Solvent | Maximum sulfone solubility (wt/wt % at 23° C.) |
|---|---|---|
| Example 1: [structure: 4-isopropylphenyl and thienyl substituted dioxo-thiapyran with dicyanomethylidene] | toluene | 4.6 |
| Example 1: [same structure] | dichloromethane | 13.5 |
| Example 2: [structure: 4-isopropylphenyl and phenyl substituted dioxo-thiapyran with dicyanomethylidene] | toluene | 12 |
| Example 2: | dichloro- | >15 |

TABLE 1-continued

Solubility of Sulfones (Saturated Solutions)

| Example or Comparative Ex: Compound | Solvent | Maximum sulfone solubility (wt/wt % at 23° C.) |
|---|---|---|
| [structure: 2,6-diaryl-4-dicyanomethylene thiopyran-1,1-dioxide with 4-isopropylphenyl and phenyl groups] | methane | |
| Comparative Example A: PTS [structure: 2,6-diaryl-4-dicyanomethylene thiopyran-1,1-dioxide with phenyl and 4-methylphenyl groups] | toluene | 2 |
| Comparative Example A: PTS [structure: same as above] | dichloromethane | 6.5 |
| Comparative Example B [structure: 2,6-bis(4-alkylphenyl)-4-dicyanomethylene thiopyran-1,1-dioxide with 4-methylphenyl and 4-ethylphenyl groups] | dichloromethane | 4.7 |
| Comparative Example C [structure: 2-(5-methylthienyl)-6-(4-ethylphenyl)-4-dicyanomethylene thiopyran-1,1-dioxide] | dichloromethane | 4.7 |

EXAMPLES 3–5

In Examples 3–5, electrophotographic elements of the invention containing the sulfone of Example 1:

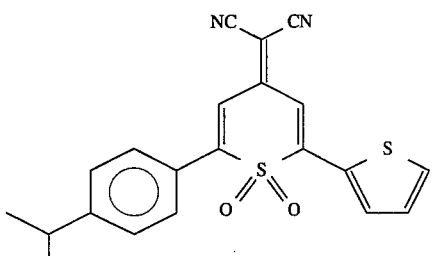

in the CTL were prepared by the following procedure:

A thin conductive layer of aluminum was vacuum-deposited on a 178 μm-thick film of polyethylene terephthalate. The aluminum-coated film was then overcoated by electron-beam evaporation with a 500-angstrom-thick layer of silicon dioxide prior to application of a charge-generation layer.

A charge-generation layer (CGL) was prepared by dispersing 2 parts by weight of titanyl tetrafluorophthalocyanine (described in U.S. Pat. No. 4,701,396), a charge-generation material, in a solution of 1 part by weight of a polymeric binder, comprising a polyester formed from 4,4'-(2-norbornylidene)diphenol and terephthalic acid-azelaic acid (40:60 molar ratio) in dichloromethane, ball milling the dispersion for 60 hours, diluting with a mixture of dichloromethane and 1,1,2-trichloroethane (final weight ratio of dichloromethane:trichloroethane was 85:15) to achieve suitable coating viscosity, coating the dispersion on the conductive layer, and evaporating the solvent to yield a CGL of 1.2 mm thickness.

A coating solution for forming a charge-transport layer (CTL) comprising 10 weight percent solids in dichloromethane was then prepared. The solids comprised the sulfone of Example 1 and a polymeric binder comprising a polyester formed from 4,4'-(2-norbornilidene) diphenol and terephthalic acid: azelaic acid (40:60 molar ratio). The sulfone of Example 1 comprised 20, 30, and 40 weight percent (Examples 3, 4, 5, respectively) of the total of polymer binder and sulfone in the coating solution. The solution was then coated over the CGL using a 5 mil doctor blade to form the CTL on the CGL. The combined thickness of the CGL and CTL was about 5 to 10 μm.

Electrophotographic sensitivity of the elements so prepared was determined by first electrostatically corona-charging each element to a uniform initial positive potential, then exposing the elements to a simulated imaging exposure, that is, an exposure to actinic radiation (radiation having peak intensity at a wavelength to which the charge-generation material in the elements is sensitive in order to generate electron-hole pairs in the CGL) in amounts sufficient to discharge 50% and 80% of the initial voltage. Electrophotographic sensitivity was measured in terms of the amount of incident actinic radiant energy (expressed in ergs/cm$^2$) needed to discharge the initial voltage down to the desired level. The lower the amount of radiation needed to achieve the desired degree of discharge, the higher is the electrophotographic sensitivity of the element, and vice versa. Each of the uniformly charged elements was subjected to radiation at a wavelength of about 830 nm, at a rate of about 2 ergs per cm$^2$ of element surface per second through the outer surface of the CTL, and then measuring the values for 50% discharge (also referred to as "half discharge", "E(V$_o$, 50%)", and "E(V$_o$, ½)") and 80% discharge (also referred to as "E(V, 80%)").

Dark decay properties were determined by measuring the dark decay (expressed in volts/second), that is, the rate of dissipation of the initial uniform voltage while the elements remained in darkness, i.e., before any exposure to actinic radiation. This was accomplished by first corona charging in the same manner as in the above sensitivity measurements, followed by measuring the initial voltage and the voltage remaining in the element after 2 seconds in darkness and dividing the difference by 2. The lower the rate of discharge in darkness, the better is the dark decay property of the elements, i.e., the better their ability to retain their initial potential before exposure.

Results are presented in Table 2. "Charge transport agent wt %" refers to the percent by weight of electron-transport agent employed, based on the total weight of polymeric binder and electron-transport agent, included in the solution used to coat the CTL of the element. "Dark decay" refers to the rate of dark decay of the elements, prior to exposure to actinic radiation, measured in volts/second (V/s) as described above. "E(V$_o$ 50%)" refers to the amount of incident actinic radiant energy, expressed in ergs/cm$^2$, needed to discharge 50% of the initial voltage, V$_o$. "E(V$_o$80%)" refers to the amount of actinic radiant energy needed to discharge 80% of V$_o$.

Electron mobility was measured by the time-of-flight method as generally discussed in Borsenberger, P. M., and Weiss, D. S., Organic Photoreceptors for Imaging Systems, Marcel Dekker, Inc., New York, 1993, p. 279 and as described in more detail in U.S. Pat. No. 5,300,385 to Detty et al, except that the substrate electrode was aluminum and the CTL thickness ranged from 6.9 to 10.6 micrometers. In samples containing 20 and 30 weight percent of the sulfone of Example 1 (Examples 3 and 4), the electron mobility was approximately the same as in samples containing equal weight percentages of PTS. For example, at a field strength of 2×10$^5$ V/cm, the mobility in Example 4 (a sample containing 30 weight percent of the sulfone of Example 1) was 1.0×10$^{-7}$ cm$^2$/V.sec. This compares to a mobility of 0.6×10$^{-7}$ cm$^2$/V.sec for PTS at the same field strength.

EXAMPLES 6–8

In Examples 6–8, the procedures of Examples 3–5 were repeated for the sulfone of Example 2:

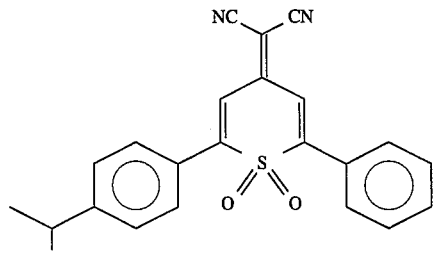

Results as to electrophotographic exposure for half discharge, 80% discharge, and dark decay were comparable to the results for Examples 3–5.

COMPARATIVE EXAMPLES D–F

In Comparative Examples D–F, the procedures of Examples 3–5 were followed with the exception that the solids contained 20, 30, and 40 weight percent PTS in place of the sulfone of Example 1. Electrophotographic exposure results are presented in Tables 2.

TABLE 2

Electrophotographic Exposure for Half Discharge, 80% Discharge, and Dark Decay for Examples 3–5 and Comparative Examples

| Ex. or Comp. Ex. | Charge transport agent wt % | $E(V_o, 50\%)$ ergs·cm$^{-2}$ | $E(V_o, 80\%)$ ergs·cm$^{-2}$ | Dark Decay V/s |
|---|---|---|---|---|
| Ex. 3 | 20% | 9.1 | 43 | 3.0 |
| Comp. Ex. D | 20% | 8.2 | 33 | 3.2 |
| Ex. 4 | 30% | 7.3 | 28 | 2.4 |
| Comp. Ex. E | 30% | 6.9 | 26 | 3.9 |
| Ex. 5 | 40% | 6.5 | 21 | 2.2 |
| Comp. Ex. F | 40% | 6.5 | 23 | 2.2 |

EXAMPLES 9a–9g and 10a–10g

Electrophotographic elements were prepared in substantially the same manner as in Examples 3–5, with the exception that Examples 9a–9g each used as charge transport agent:

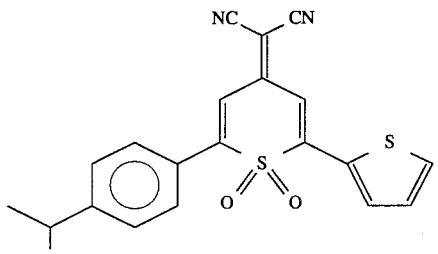

and Examples 10a–10g each used as charge transport agent:

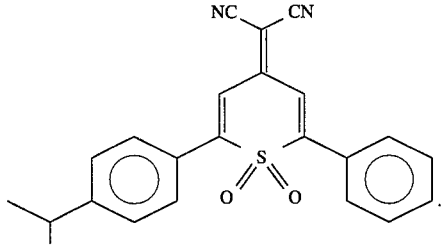

The relative concentrations of charge transport agent and binder (in parts by weight) were varied as indicated in Table 3. Each element was examined to determine the extent of crystallization of the charge transport agent in the element. Crystallization visible without magnification extending over less than 5 percent of the element was considered acceptable. Visible crystallization extending over more than 5 percent of the element was considered unacceptable. Results are presented in Table 3.

COMPARATIVE EXAMPLES G1–G7

The procedures of Examples 9a–9g and 10a–10g were followed except PTS was substituted for the indicated sulfones. Results are presented in Table 3.

TABLE 3

ACCEPTABLE COMPATIBILITY OF CHARGE TRANSPORT AGENT AND BINDER IN ELECTROPHOTOGRAPHIC ELEMENT

| SULFONE:BINDER RATIO (Wt. %/Wt. %) | Comparative Examples G | Examples 9 | Example 10 |
|---|---|---|---|
| 60/40 | G1: YES | 9a: YES | 10a: YES |
| 65/35 | G2: YES | 9b: YES | 10b: YES |
| 70/30 | G3: NO | 9c: YES | 10c: YES |
| 75/25 | G4: NO | 9d: YES | 10d: YES |
| 80/20 | G5: NO | 9e: NO | 10e: YES |
| 85/15 | G6: NO | 9f: NO | 10f: YES |
| 90/10 | G7: NO | 9g: NO | 10g: NO |

Tables 1 and 3 illustrate the surprising nature of the solubility and compatibility characteristics of the sulfones of the invention. Solubilities vary greatly between the compounds of the indicated Examples and Comparative Examples despite what would otherwise appear to be minor differences in chemical structure. Table 2 illustrates that elements including the sulfones of the invention have electrophotographic characteristics, including dark decay and sensitivity, at least comparable to PTS. Examples 1–2 and 9–10 illustrate the very high charge transport agent loading possible with the sulfones of the invention.

The invention has been described in detail with particular reference to certain preferred embodiments thereof, but it should be appreciated that variations and modifications can be effected within the spirit and scope of the invention.

What is claimed is:

1. A multilayered electrophotographic element wherein at least one of said layers includes polymeric binder and a charge transport agent having the general structure

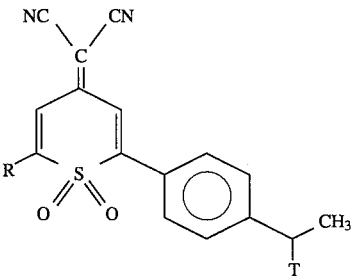

wherein R is selected from the group consisting of alkyl and cycloalkly groups having from 1 to about 10 carbons, aryl and heteroaryl groups having a total of carbons and heteroatoms of from 6 to about 12, a furyl group, a selenophene group, and a thienyl group; and T is alkyl having from 1 to 4 carbons.

2. The electrophotographic element of claim 1 wherein said charge transport agent is more compatible with said polymeric binder than is 4-dicyanomethylene-2-p-tolyl-6-phenyl-4H-thiopyran-1,1-dioxide.

3. The electrophotographic element of claim 2 wherein said charge transport agent is from about 20 to 70 weight percent of the total of said charge transport agent and said polymeric binder.

4. The electrophotographic element of claim 1 wherein R is an aryl or heteroaryl group having a total of carbons and heteroatoms of from 6 to about 12 and T is alkyl having from 1 to 4 carbons.

5. The electrophotographic element of claim 1 wherein said polymeric binder is selected from the group consisting of styrene-butadiene copolymers; vinyltoluene-styrene copolymers; styrene-alkyd resins; silicone-alkyd resins; soya-alkyd resins; vinylidene chloride-vinyl chloride copolymers; poly(vinylidene chloride); vinylidene chloride-acrylonitrile copolymers; vinyl acetate-vinyl chloride copolymers; poly(vinyl acetals); nitrated polystyrene; poly(methylstyrene); isobutylene polymers; polyesters; phenol-formaldehyde resins; ketone resins; polyamides; polycarbonates; polythiocarbonates; poly-[ethylene-co-isopropylidene-2,2-bis(ethyleneoxy-phenylene)terephthalate]; copolymers of vinyl haloacrylates and vinyl acetate; chlorinated polyolefins; and polyimides.

6. The electrophotographic element of claim 1 wherein T is methyl or ethyl.

7. The electrophotographic element of claim 1 wherein R is phenyl or thienyl.

8. The electrophotographic element of claim 1 wherein said charge transport agent is selected from the group consisting of

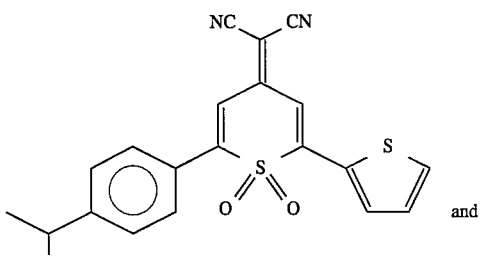

and

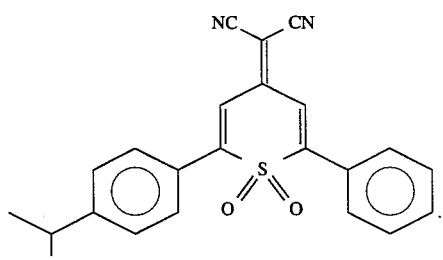

9. The electrophotographic element of claim 1 further characterized as having one layer having the primary function of charge generation and having another layer having the primary function of charge transport.

10. An electrophotographic element comprising an electrically conductive layer, a charge generating layer, and a layer including a polymeric binder and a charge transport agent having the general structure

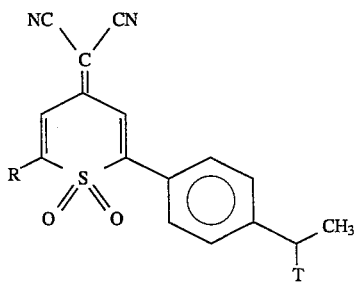

wherein R is selected from the group consisting of aryl and heteroaryl groups having a total of carbons and heteroatoms of from 6 to about 12, a furyl group, a selenophene group and a thienyl group; and T is alkyl having from 1 to 4 carbons.

11. The electrophotographic element of claim 10 wherein said layer including said charge transport agent further includes a polymeric binder and said charge transport agent is greater than 50 weight percent of the total of said charge transport agent and said polymeric binder and said layer is substantially free of zones of incompatibility.

12. The electrophotographic element of claim 11 wherein said layer including said charge transport agent further includes a polymeric binder and said charge transport agent is more compatible with said polymeric binder than is 4-dicyanomethylene-2-p-tolyl-6-phenyl-4H-thiopyran-1,1-dioxide and said polymeric binder is selected from the group consisting of styrene-butadiene copolymers; vinyltoluene-styrene copolymers; styrene-alkyd resins; silicone-alkyd resins; soya-alkyd resins; vinylidene chloride-vinyl chloride copolymers; poly(vinylidene chloride); vinylidene chloride-acrylonitrile copolymers; vinyl acetate-vinyl chloride copolymers; poly(vinyl acetals); nitrated polystyrene; poly(methylstyrene); isobutylene polymers; polyesters; phenol-formaldehyde resins; ketone resins; polyamides; polycarbonates; polythiocarbonates; poly-[ethylene-co-isopropylidene-2,2-bis(ethyleneoxy-phenylene)terephthalate]; copolymers of vinyl haloacrylates and vinyl acetate; chlorinated polyolefins; and polyimides.

13. The electrophotographic element of claim 12, wherein R is phenyl or thienyl.

14. The electrophotographic element of claim 13 wherein T is methyl or ethyl.

15. An electrophotographic element comprising in a polymeric binder a compound having the structure

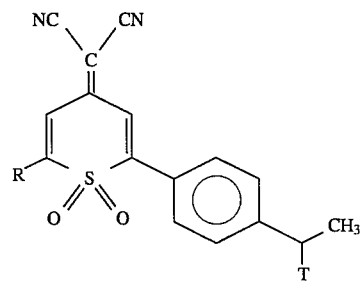

wherein R is substituted or unsubstituted and is selected from the group consisting of alkyl and cycloalkyl groups having from 1 to about 10 carbons, aryl and heteroaryl groups having a total of carbons and heteroatoms of from 6 to about 12, a furyl group, a selenophene group, and a thienyl group; and T is alkyl having from 1 to 4 carbons.

16. The electrophotographic element of claim 15 wherein T is methyl or ethyl.

17. The electrophotographic element of claim 15 wherein R is phenyl or thienyl.

18. The electrophotographic element of claim 15 wherein said charge transport agent is selected from the group consisting of

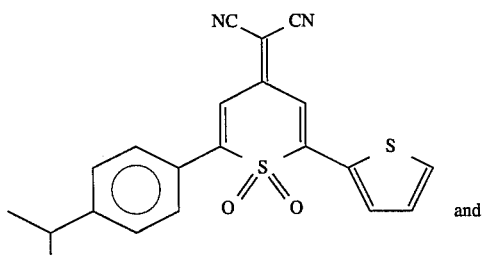

and

-continued
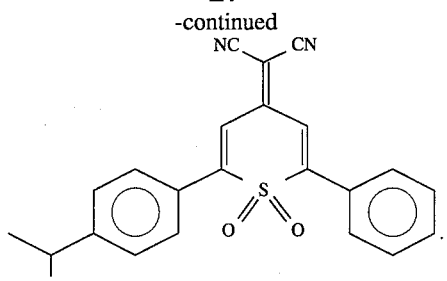
19. The electrophotographic element of claim 15 wherein R is selected from the group consisting of a furyl group, a selenophene group and thienyl group.
20. The electrophotographic element of claim 15 wherein R is substituted by alkyl having from 1 to about 12 carbons, alkoxy having from 1 to about 12 carbons, nitro, cyano, dialkylamino, arylalkylamino or diarylamine.
* * * * *